(12) United States Patent
Cunningham et al.

(10) Patent No.: US 8,968,289 B2
(45) Date of Patent: Mar. 3, 2015

(54) MICROWAVE SPACERS AND METHODS OF USE

(75) Inventors: Robert B. Cunningham, Longmont, CO (US); Gene H. Arts, Berthoud, CO (US); Timothy A. Turley, Highlands Ranch, CO (US); Richard W. Wetz, Erie, CO (US); Chad M. Nelson, Louisville, CO (US)

(73) Assignee: Covidien LP, Mansfield, MA (US)

( * ) Notice: Subject to any disclaimer, the term of this patent is extended or adjusted under 35 U.S.C. 154(b) by 1158 days.

(21) Appl. No.: 12/910,442

(22) Filed: Oct. 22, 2010

(65) Prior Publication Data

US 2012/0101487 A1    Apr. 26, 2012

(51) Int. Cl.
*A61B 18/18* (2006.01)
*A61B 17/34* (2006.01)

(52) U.S. Cl.
CPC ..... *A61B 18/1815* (2013.01); *A61B 2018/1869* (2013.01); *A61B 2017/3411* (2013.01)
USPC .................................. 606/33; 606/34; 606/35

(58) Field of Classification Search
USPC ....................................... 606/32–45; 604/116
See application file for complete search history.

(56) References Cited

U.S. PATENT DOCUMENTS

| | | | |
|---|---|---|---|
| 3,631,363 A | 12/1971 | Miller | |
| D223,367 S | 4/1972 | Kountz | |
| D266,842 S | 11/1982 | Villers et al. | |
| 4,397,313 A | 8/1983 | Vaguine | |
| 4,462,412 A | 7/1984 | Turner | |
| D278,306 S | 4/1985 | McIntosh | |
| 4,572,190 A | 2/1986 | Azam et al. | |
| 4,608,977 A | 9/1986 | Brown | |
| 4,662,368 A | 5/1987 | Hussein et al. | |
| 4,798,215 A | 1/1989 | Turner | |
| 4,848,196 A | 7/1989 | Roberts | |

(Continued)

FOREIGN PATENT DOCUMENTS

| DE | 390937 | 3/1924 |
|---|---|---|
| DE | 1099658 | 2/1961 |

(Continued)

OTHER PUBLICATIONS

U.S. Appl. No. 08/483,742, filed Jun. 7, 1995, Roger A. Stern.

(Continued)

*Primary Examiner* — Linda Dvorak
*Assistant Examiner* — Amanda Scott

(57) ABSTRACT

Disclosed is a spacer, configured to position microwave energy delivery devices, including a housing, with a housing body and a compression body, and at least one compression mechanism. The housing body forms a housing body cavity and a plurality of housing device apertures. The compression body forms a plurality of compression body apertures that each correspond to a housing device aperture. The compression body slideably engages the housing body cavity and at least a portion of the compression body is positioned within the compression body cavity. A compression mechanism is positioned between the housing body and the compression body and configured to provide a biasing force between the housing body and the compression body. In a first position the housing device apertures are misaligned with the compression body apertures and in the second position the housing apertures are aligned with the compression body apertures forming a plurality of aligned apertures.

19 Claims, 7 Drawing Sheets

(56) References Cited

U.S. PATENT DOCUMENTS

| | | |
|---|---|---|
| 4,907,589 A | 3/1990 | Cosman |
| 5,097,844 A | 3/1992 | Turner |
| 5,099,846 A | 3/1992 | Hardy |
| 5,197,466 A | 3/1993 | Marchosky et al. |
| 5,284,144 A | 2/1994 | Delannoy et al. |
| 5,323,778 A | 6/1994 | Kandarpa et al. |
| 5,323,779 A | 6/1994 | Hardy et al. |
| D354,218 S | 1/1995 | Van de Peer |
| 5,383,876 A | 1/1995 | Nardella |
| 5,403,311 A | 4/1995 | Abele et al. |
| 5,417,210 A | 5/1995 | Funda et al. |
| 5,458,597 A | 10/1995 | Edwards et al. |
| 5,623,931 A | 4/1997 | Wung et al. |
| 5,626,607 A | 5/1997 | Malecki et al. |
| 5,924,992 A | 7/1999 | Park et al. |
| 6,031,375 A | 2/2000 | Atalar et al. |
| D424,693 S | 5/2000 | Pruter |
| 6,241,725 B1 | 6/2001 | Cosman |
| 6,267,770 B1 | 7/2001 | Truwit |
| 6,277,116 B1 | 8/2001 | Utely et al. |
| 6,296,639 B1 | 10/2001 | Truckai et al. |
| 6,331,166 B1 | 12/2001 | Burbank et al. |
| 6,355,033 B1 | 3/2002 | Moorman et al. |
| 6,375,606 B1 | 4/2002 | Garibaldi et al. |
| 6,428,486 B2 | 8/2002 | Ritchart et al. |
| 6,451,015 B1 | 9/2002 | Rittman, III et al. |
| 6,508,786 B2 | 1/2003 | Huitema |
| 6,513,423 B2 | 2/2003 | Thomas |
| 6,530,922 B2 | 3/2003 | Cosman et al. |
| 6,564,806 B1 | 5/2003 | Fogarty et al. |
| 6,579,262 B1 | 6/2003 | Mick |
| 6,603,994 B2 | 8/2003 | Wallace et al. |
| 6,628,990 B1 | 9/2003 | Habib et al. |
| 6,652,520 B2 | 11/2003 | Moorman et al. |
| D487,039 S | 2/2004 | Webster et al. |
| 6,725,080 B2 | 4/2004 | Melkent et al. |
| 7,008,421 B2 | 3/2006 | Daniel et al. |
| 7,197,363 B2 | 3/2007 | Prakash et al. |
| 7,223,264 B2 | 5/2007 | Daniel et al. |
| 7,226,446 B1 | 6/2007 | Mody et al. |
| 7,278,991 B2 | 10/2007 | Morris et al. |
| 7,282,049 B2 | 10/2007 | Orszulak et al. |
| 7,335,198 B2 | 2/2008 | Eggers et al. |
| 7,341,586 B2 | 3/2008 | Daniel et al. |
| D576,932 S | 9/2008 | Strehler |
| 7,422,586 B2 | 9/2008 | Morris et al. |
| 7,439,736 B2 | 10/2008 | Meaney et al. |
| 7,452,331 B1 | 11/2008 | Pruter |
| 7,467,015 B2 | 12/2008 | Van der Weide |
| D594,736 S | 6/2009 | Esjunin |
| D594,737 S | 6/2009 | Kelly et al. |
| 7,553,309 B2 | 6/2009 | Buysse et al. |
| 7,565,207 B2 | 7/2009 | Turner et al. |
| 7,625,371 B2 | 12/2009 | Morris et al. |
| 7,642,451 B2 | 1/2010 | Bonn |
| D613,412 S | 4/2010 | DeCarlo |
| 7,697,972 B2 | 4/2010 | Verard et al. |
| 7,875,024 B2 | 1/2011 | Turovskiy et al. |
| 2002/0022836 A1 | 2/2002 | Goble et al. |
| 2003/0032951 A1 | 2/2003 | Rittman, III et al. |
| 2004/0242992 A1 | 12/2004 | Hareyama |
| 2004/0267256 A1 | 12/2004 | Garabedian et al. |
| 2005/0149101 A1 | 7/2005 | Huschmand Nia |
| 2006/0015161 A1 | 1/2006 | Longo et al. |
| 2006/0122581 A1 | 6/2006 | Ein-Gal |
| 2006/0142757 A1 | 6/2006 | Daniel et al. |
| 2007/0203480 A1 | 8/2007 | Mody et al. |
| 2008/0021448 A1 | 1/2008 | Orszulak et al. |
| 2008/0183165 A1 | 7/2008 | Buysse et al. |
| 2008/0262424 A1 | 10/2008 | van't Hooft |
| 2009/0076497 A1 | 3/2009 | Morris et al. |
| 2009/0138005 A1 | 5/2009 | Prakash et al. |
| 2009/0171203 A1 | 7/2009 | Avital et al. |
| 2009/0187180 A1 | 7/2009 | Brannan |
| 2009/0192510 A1 | 7/2009 | Bahney |
| 2009/0198226 A1 | 8/2009 | Prakash et al. |
| 2009/0198227 A1 | 8/2009 | Prakash |
| 2009/0222002 A1 | 9/2009 | Bonn et al. |
| 2009/0248005 A1 | 10/2009 | Rusin et al. |
| 2009/0248006 A1 | 10/2009 | Paulus et al. |
| 2009/0264877 A1 | 10/2009 | DeCarlo |
| 2009/0295674 A1 | 12/2009 | Bonn |
| 2009/0306652 A1 | 12/2009 | Buysse et al. |
| 2009/0306659 A1 | 12/2009 | Buysse |
| 2009/0326620 A1 | 12/2009 | Rossetto et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0036379 A1 | 2/2010 | Prakash et al. |
| 2010/0045558 A1 | 2/2010 | Rossetto |
| 2010/0045559 A1 | 2/2010 | Rossetto |
| 2010/0049185 A1 | 2/2010 | Paulus |
| 2010/0049193 A1 | 2/2010 | Huseman |
| 2010/0053015 A1 | 3/2010 | Willyard |
| 2010/0057070 A1 | 3/2010 | Behnke et al. |
| 2010/0076422 A1 | 3/2010 | Podhajsky |
| 2010/0082082 A1 | 4/2010 | Prakash et al. |
| 2010/0087808 A1 | 4/2010 | Paulus |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0101825 A1 | 4/2010 | Bonn |
| 2010/0217251 A1 | 8/2010 | Rossetto et al. |
| 2010/0217252 A1 | 8/2010 | Rossetto et al. |
| 2010/0234839 A1 | 9/2010 | Smith et al. |
| 2010/0256624 A1 | 10/2010 | Brannan et al. |
| 2010/0262134 A1 | 10/2010 | Jensen et al. |
| 2010/0286681 A1 | 11/2010 | Podhajsky |
| 2010/0286682 A1 | 11/2010 | Podhajsky |
| 2010/0286683 A1 | 11/2010 | Podhajsky |
| 2010/0305559 A1 | 12/2010 | Brannan et al. |
| 2010/0305560 A1 | 12/2010 | Peterson |
| 2010/0305561 A1 | 12/2010 | Prakash et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |

(56) References Cited

FOREIGN PATENT DOCUMENTS

| | | |
|---|---|---|
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 070 518 | 1/2001 |
| EP | 1 159 926 | 5/2001 |
| EP | 1 186 274 | 3/2002 |
| EP | 1 278 007 | 1/2003 |
| EP | 1 645 234 | 4/2006 |
| EP | 1 645 235 | 4/2006 |
| EP | 1800712 | 6/2007 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| GB | 2242132 | 9/1991 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO99/04710 | 2/1999 |
| WO | WO99/56812 | 11/1999 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO03/088858 | 10/2003 |
| WO | WO2004/017851 | 3/2004 |
| WO | WO2004/112628 | 12/2004 |
| WO | WO2005/009528 | 2/2005 |
| WO | WO2005/016119 | 2/2005 |

OTHER PUBLICATIONS

U.S. Appl. No. 08/136,098, filed Oct. 14, 1993, Roger A. Stern.
U.S. Appl. No. 12/536,616, filed Aug. 6, 2009, Arnold v. DeCarlo.
U.S. Appl. No. 12/877,182, filed Sep. 8, 2010, Robert B. Cunningham.
U.S. Appl. No. 12/910,442, filed Oct. 22, 2010, Robert B. Cunningham.
U.S. Appl. No. 60/405,051, filed Aug. 21, 2002, Daniel et al.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.

(56) References Cited

OTHER PUBLICATIONS

E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages (2004).
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
S. Humphries Jr. et al., "Finite•Element Codes to Model Electrical Heating and Non•Llnear Thermal Transport in Biological Media", Proc. ASME HTD-355, 131 (1997).
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.

(56) References Cited

OTHER PUBLICATIONS

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'VOA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.

(56) References Cited

OTHER PUBLICATIONS

International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/USO4/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report for European Application No. 11008506.5 dated Jan. 18, 2012.
Office Action from European Application No. 11 008 506.5 dated Jul. 9, 2013.

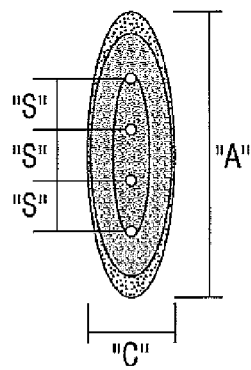
FIG. 1A
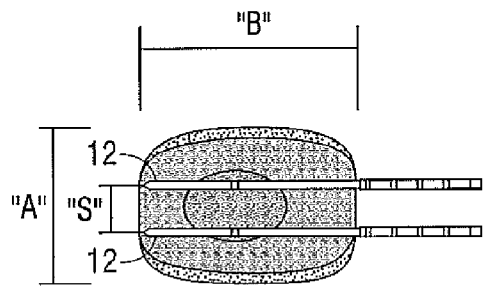
FIG. 1B
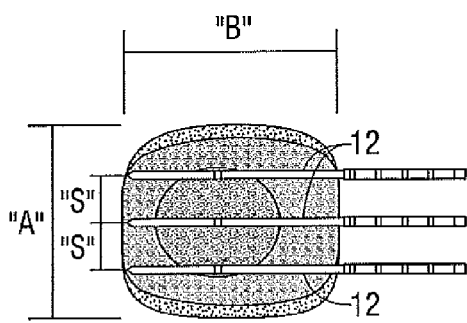
FIG. 1C
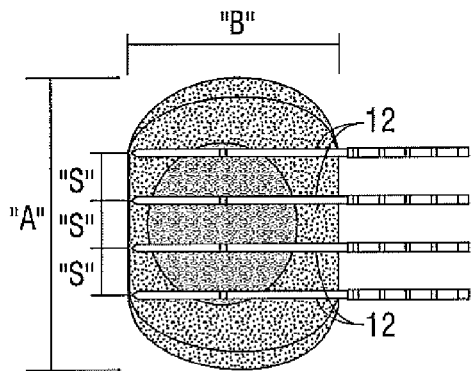
FIG. 1D
|   | Number of Antennas | | |
|---|---|---|---|
|   | Two | Three | Four |
| S | 1.0 cm | 1.0 cm | 1.0 cm |
| A | 2.4 cm | 3.3 cm | 4.4 cm |
| B | 3.4 cm | 3.4 cm | 3.4 cm |
| C | 1.7 cm | 1.7 cm | 1.7 cm |
FIG. 1E

MICROWAVE SPACERS AND METHODS OF USE

BACKGROUND

1. Technical Field

The present disclosure relates to apparatuses, systems and methods for providing energy to biological tissue and, more particularly, apparatuses, systems and methods for precise placement of microwave energy delivery devices during a surgical procedure.

2. Background of Related Art

Energy-based tissue treatment is well known in the art. Various types of energy (e.g., electrical, ultrasonic, microwave, cryogenic, thermal, laser, etc.) may be applied to tissue to achieve a desired result. Electrosurgery involves application of high radio-frequency electrical current to a surgical site to cut, ablate, coagulate or seal tissue. In monopolar electrosurgery, a source or active electrode delivers radio-frequency energy from the electrosurgical generator at a predetermined frequency to the tissue and a return electrode carries the current back to the generator. In monopolar electrosurgery, the source electrode is typically part of the surgical instrument held by the surgeon and applied to the tissue to be treated and a patient return electrode is placed remotely from the active electrode to carry the current back to the generator. In bipolar electrosurgery, the active and return electrodes are placed in close proximity to each other, e.g., at the surgical site, and electrosurgical currents are passed therebetween. In microwave electrosurgery, the antenna of the microwave energy delivery device generates electromagnetic fields in the adjacent tissue without the generation of electrosurgical currents between an active electrode and a return electrode as discussed hereinabove.

Radio-frequency energy may be delivered to targeted tissue in an ablation procedure by electrosurgical probes or by an electrosurgical antenna. In the case of tissue ablation using electrosurgical probes, electrode pairs are positioned in the surgical site to delivery high frequency electrosurgical currents between the pairs of active (+) and return (−) electrodes. An active (+) electrode and a return (−) electrode may be positioned in a spaced apart relationship on the shaft of an electrosurgical probe such that electrosurgical currents are passed along, or parallel to the shaft.

Alternatively, a first probe may function as an active (+) electrode and a second probe may function as a return (−) electrode. The first and second probes are positioned in a spaced apart relationship relative to each other such that electrosurgical currents are passed between the active (+) and return (−) electrodes resulting in the ablation of tissue positioned between the two probes. As such, the ablation region is defined by the spacing between the active (+) and return (−) electrodes and heating of tissue is typically confined therebetween. During ablation, current pathways in tissue between the active (+) and return (−) electrode produce localized heating between the two probes.

Radio-frequency energy in a microwave frequency range may be delivered to a targeted tissue by a microwave energy delivery device with a microwave antenna on the distal tip. The antenna of the microwave energy delivery device, when provided with a microwave energy signal, generates electromagnetic fields in the adjacent tissue without the generation of electrosurgical currents between an active electrode and a return electrode as discussed hereinabove.

While the ablation region produced by ablation probes is defined by the current path between the electrodes, the ablation region (shape and volume) produced by a microwave energy delivery device is defined by the type of antenna, the frequency of the microwave energy signal and the power level of the microwave energy signal. For example, an ablation region generated by a microwave energy delivery device may be symmetric about the tip and shaft of the microwave energy delivery device, directed to only one side of the shaft or if the antenna is unchoked, the ablation region may include a "tail" portion that extends proximally along the elongated shaft of the microwave energy delivery device.

Unlike radio-frequency probes, microwave energy delivery devices need not be configured to interact with each other. In fact, microwave energy delivery devices typically do not interact since any interaction would be due to the intermingling of the electromagnetic fields generated by the two devices (i.e., the two devices placed in close proximity may result in the overlapping of electromagnetic fields generated by each microwave energy delivery device). The overlapping electromagnetic fields may result in unpredictable results as the electromagnetic fields may cancel each other (resulting in no heating), the electromagnetic fields may combine (resulting in the generation of pockets of extremely high field densities) or any combination thereof. As such, controlling the spacing, and therefore controlling the interaction between microwave energy delivery devices becomes even more critical when the surgical procedures requires the insertion of a plurality of microwave energy delivery devices.

The unpredictable nature of the overlapping electromagnetic fields can be overcome by precisely placing the microwave energy delivery devices in a target tissue.

SUMMARY

Disclosed is a spacer configured to position microwave energy delivery devices including a housing, with a housing body, a compression body, and at least one compression mechanism. The housing body forms a housing body cavity and a plurality of housing device apertures. The compression body forms a plurality of compression body apertures that each correspond to a housing device aperture. The compression body is configured to slideably engage the housing body cavity and at least a portion of the compression body is positioned within the compression body cavity. A compression mechanism is positioned between the housing body and the compression body and configured to provide a biasing force between the housing body and the compression body. In a first position the housing device apertures are misaligned with the compression body apertures and in the second position the housing apertures are aligned with the compression body apertures and form a plurality of aligned apertures configured to receive a microwave energy delivery device therethrough.

In a third position the housing body and the compression body apply a biasing force, generated from the compression mechanism, to any microwave energy delivery device positioned through one of the plurality of aligned aperture pairs.

The compression mechanism may further include one or more springs positioned between the compression body and the housing body wherein in the first position the spring is substantially uncompressed and in the second position a spring is substantially compressed.

In a further embodiment, the spacer further includes a middle portion, configured to slideably engage a compression body cavity formed in the compression body, and a second compression mechanism. The middle portion forms a middle device aperture therein and the second compression mechanism, positioned between the middle portion and the housing body, provide a second biasing force between the middle portion and the housing body. In the first position the housing device apertures are misaligned with the middle device aperture and in the second position at least one of the plurality of housing device apertures is aligned with the middle device aperture and forms a middle device aperture configured to receive the microwave energy delivery device therethrough.

The first compression mechanism may include a first compression mechanism spring positioned between the compression body and the housing body. In the first position the first compression mechanism spring is substantially uncompressed and in the second position the first compression mechanism spring is substantially compressed.

The second compression mechanism may include a second compression mechanism spring positioned between the housing body and the middle portion. In the first position the second compression mechanism spring is substantially uncompressed and in the second position the second compression mechanism spring is substantially compressed. In a third position the housing body and the compression body are configured to apply a first biasing force to the microwave energy delivery device positioned through an aligned aperture pairs and the housing body and the middle portion are configured to apply a second biasing force to the microwave energy delivery device positioned through the middle device aperture.

In yet another embodiment the first compression mechanism includes two first compression mechanism springs positioned between the compression body and the housing body and the second compression mechanism includes a one second compression mechanism spring positioned between the housing body and the middle portion. In the first position, the second compression mechanism spring and the two first compression mechanism springs are substantially uncompressed and in the second position the second compression mechanism spring and the two first compression mechanism springs are substantially compressed. In a third position, the compression body and the housing body are configured to apply a first biasing force to the microwave energy delivery device positioned through one of the plurality of aligned aperture pairs and the housing body and the middle portion are configured to apply a second biasing force to the microwave energy delivery device positioned through the middle device aperture. The first biasing force and the second biasing force may not be equal.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 1A-1D are perspective views of various arrangements of microwave energy delivery device spacing and the resulting ablation region generated thereby;

FIG. 1E is a table providing measurements of the ablation regions generated from the arrangements illustrated in FIGS. 1B-1D;

DETAILED DESCRIPTION

Figure 3:
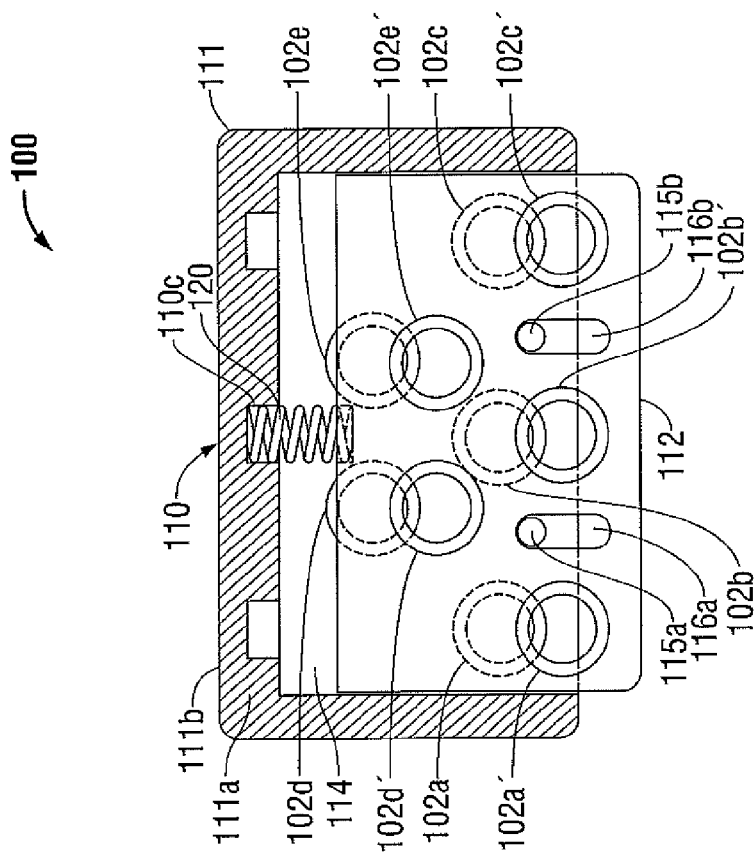
FIG. 3 is a perspective view of the microwave spacer in FIG. 2, illustrating a spring-driven compression mechanism.

Particular embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

FIGS. 1A-1D show perspective views of various arrangements of the antennas 12 of microwave energy delivery devices and the resulting ablation regions generated thereby. The spacing between two adjacent antennas 12 is illustrated by a measurement of "S" and the length, depth and width of an ablation region generated by an ablation procedure is illustrated by a measurement of "A", "B" and "C", respectively.

Table 1, as illustrated in FIG. 1E, provides measurements of the ablation regions generated from the arrangements illustrated in FIGS. 1B-1D during an actual ablation procedure. In each procedure, the antennas 12 deliver microwave energy at a frequency of about 915 MHz for two minutes at a power level of 45 watts using tissue penetrating microwave energy delivery devices 10 sold by Covidien under the trademark Evident™ MW Ablation Surgical Antennas and Evident™ MW Ablation Surgical Antennas.

The illustrations in FIGS. 1A-1D and the measurements of an ablation region for the three configurations provided in Table 1 demonstrates that the addition of each antenna 12 incrementally increases the length of the ablation region (e.g., dimension "A"). As such, a clinician can control the size of the generated ablation region by selecting the number of antennas and by controlling the position of each antenna 12 with respect to one other.

The microwave spacers 100, 300 in accordance with the embodiments of the present disclosure are used to assist a clinician in obtaining proper spacing during an insertion step of a procedure. The microwave spacers 100, 300 may also assist the clinician in maintaining the desired spacing during a delivery step of the procedure. Finally, the microwave spacers 100, 300 may be configured to assist the clinician during the removal step of a procedure by providing a means of simultaneously removing the plurality of microwave energy delivery devices 10 from patient tissue.

Microwave spacers 100, 300 are generally constructed with geometries that are suited for a particular microwave energy delivery device 10. While the microwave spacers 100, 300 of the present disclosure are illustrated for use with a particular microwave energy delivery device 10, such as the above-mentioned Evident™ MW Ablation Surgical Antennas, the microwave spacers 100, 300 may be adapted for use with any suitable tissue penetrating microwave energy delivery device 10 that includes an antenna 12 on the distal end and require controlled spacing therebetween.

Figure 2:
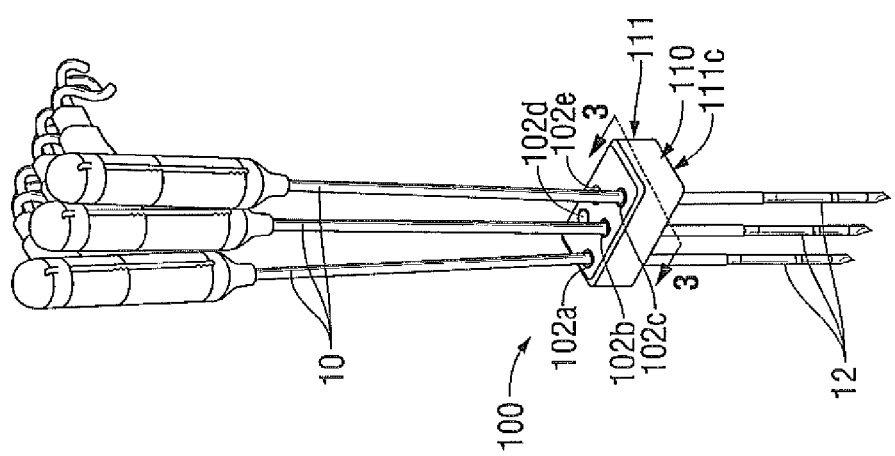
FIG. 2 is a perspective view of a microwave spacer including a compression mechanism in accordance with the present disclosure positioning three microwave energy delivery devices in a straight line configuration.

FIG. 2 is a perspective view of a microwave spacer 100, in accordance with one embodiment of the present disclosure. The microwave spacer 100 provides even spacing between three microwave energy delivery devices 10 deployed in a straight-line configuration. Microwave spacer 100 includes a plurality of housing device apertures 102a-102e formed in a housing body 111 each configured to receive a microwave energy delivery device 10 therethrough. A portion of the compression body 112 (see FIG. 3), positioned in each of the plurality of housing device apertures 102a-102e is configured to hold and/or lock a respective microwave energy delivery device 10 to the microwave spacer 100.

The microwave spacers 100, 300 of the present disclosure are configured to arrange, align, position and/or configure the microwave energy delivery devices 10 (or any other energy delivery device) for use in a surgical procedure. While FIG. 2 illustrates a microwave spacer 100 with three microwave energy delivery devices 10 arranged in a substantially straight line, other configurations may be selected. For example, microwave spacer 100 is configured to arrange microwave energy delivery devices 10 in an equilateral triangular configuration by utilizing the appropriate apertures 102b, 102d, 102e.

While the particular microwave energy delivery devices 10 described herein were tested using a microwave spacer 100 including a spacing of 1 cm between adjacent apertures, other dimensions, sizes and/or spacing arrangements are contemplated. More particularly, a selected microwave energy delivery device 10 may operate under different power requirements and/or at different frequencies and therefore may require different sizes and spacing. As such, the size of the microwave spacer 100, the number of apertures, e.g., housing device apertures 102a-102e, and/or the spacing therebetween may be related to the particular microwave energy delivery device 10, a parameter related to energy delivered by the microwave energy delivery device 10 (i.e., power, current, voltage and/or frequency of the energy), the surgical procedure performed and/or the duration of the surgical procedure.

FIG. 3 is a perspective view of the microwave spacer 100 of FIG. 2, illustrating a compressible holding/locking mechanism in accordance with one embodiment of the present disclosure. Microwave spacer 100 includes a housing 110 including a housing body 111 and a compression body 112. The housing body 111 includes a housing body cavity 114 defined therein that slideably engages the compression body 112. Positioning dowels 115a, 115b are positioned in and engage corresponding dowel slots 116a, 116b formed in the compression body 112. Dowel slots 116a, 116b limit the travel of the compression body 112 within the housing body cavity 114 by engaging the positioning dowels 115a, 115b. Dowel slots 116a, 116b may also guide the compression body 112 within the housing body cavity 114.

In one embodiment of the present disclosure, housing body 111 may include two or more positioning dowel apertures defined therein (not explicitly shown) that align with a corresponding dowel slots 116a, 115b formed in the compression body 112. Each positioning dowel aperture is configured to receive a positioning dowel 115a, 115b therethrough. Positioning dowels 115a, 115b, once inserted into the positioning dowel apertures, may be secured within the positioning dowel apertures by any suitable holding or locking material, structure or mechanism (e.g., adhesive, epoxy, a locking tapered end, a press-fit, and/or a stepped dowel).

In another embodiment of the present disclosure, at least a portion of each positioning dowel 115a, 115b may be formed in the housing body 111. For example, the housing body 111 may include an upper housing body 111a and a lower housing body 111b that mated together form the housing body 111. The upper housing body 111a and lower housing body 111b may include upper and lower dowel appendages (not explicitly shown) that when mated together form each of the positioning dowels 115a, 115b.

During assembly, the compression body 112 and a spring 120 are positioned on the upper housing body 111a or the lower housing body 111b such that when mated together the upper and lower dowel appendages of the respective upper housing body 111a and lower housing body 111b form the positioning dowels 115a, 115b within the dowel slots 116a, 116b.

Microwave spacer 100 further includes a compression mechanism, e.g., spring 120, in the housing body cavity 114 positioned between the housing body 111 and the compression body 112. The compression mechanism is configured to resist compression of the compression body 112 into the housing body cavity 114. In one embodiment and as illustrated in FIG. 3, the compression mechanism is a spring 120 positioned in the housing body cavity 114 between the interior surface of the housing body 111 and the compression body 112. Spring 120 provides a pressure force or driving force that biases the compression body 112 to a first position within the housing body cavity 114 wherein the positioning dowels 115a, 115b are positioned to an interior position in the dowel slots 116a, 116b, respectively (see FIG. 3). In the first position, the interface between the dowel slots 116a, 116b and the positioning dowels 115a, 115b allow at least a portion of the compression body 112 to extend out of the housing body cavity 114.

Spring 120 is one example of a suitable compression mechanism. The compression mechanism may include a pneumatic pressure device, an elastic compression device, a resilient member, air bladder or any other suitable device that resists compression and/or resistance to the compression body 112 when driven into the housing body cavity 114.

Housing body 111 and compression body 112 each form a plurality of device apertures 102a-102e and 102a'-102e' therein, respectively. For each housing device aperture 102a-102e formed in the housing body 111a corresponding compression body aperture 102a'-102e' is formed in the compression body 112.

In a first position, as illustrated in FIG. 3 and discussed hereinabove, each housing device aperture 102a-102e is not in vertical alignment with the corresponding compression body aperture 102a'-102e'. By applying a compression force to the compression body 112 against the biasing force in the direction of the housing body (e.g., moving the compression body 112 into the housing body cavity 114 by squeezing the housing body 111 and compression body 112 together) the housing body 111 and compression body 112 can be positioned in a second position, wherein each housing device aperture 102a-102e aligns with a corresponding compression body aperture 102a'-102e'. In the second position, one or more microwave energy delivery devices 10 can be inserted through a selected device aperture pair 102a and 102a', 102b and 102b', 102c and 102c', 102d and 102d', 102e and 102e'.

After one or more microwave energy delivery devices 10 are positioned in a selected device aperture pair 102a and 102a', 102b and 102b', 102c and 102c', 102d and 102d', 102e and 102e', the compression body 112, when released, is biased toward the first position by the spring 120 (or other biasing device). The one or more microwave energy delivery devices 10, each positioned in a selected aperture pair (e.g., 102a and 102a') limits the travel of the compression body 112 and prevents the compression body 112 from returning to the first position. Instead, the placement of a microwave energy delivery device 10 into a selected pair of apertures (e.g, 102a and 102a') positions the compression body 112 in a third position wherein at least a portion of the compression body 112 and housing body 111 apply a biasing force (e.g., a compression force) to at least a portion of a microwave energy delivery devices 10 positioned in a selected aperture pair 102a, 102a', as illustrated in FIG. 5C. The biasing force, applied to each respective microwave energy delivery device 10 by the compression body 112 and the housing body 111, locks and/or holds the microwave energy delivery device 10 in a fixed position with respect to the microwave spacer 100.

The portion of the compression body 112 and/or the housing body 111 in contact with the microwave energy delivery device 10, positioned in the selected aperture pair 102a, 102a', may include a coating or non-slip material configured to frictionally retain the microwave energy delivery device 10, such as, for example, a light adhesive coating, a non-skid cover or any other suitable surface or coating that aids in preventing relative movement between the microwave spacer 100 and the microwave energy delivery devices 10 positioned in the selected aperture pair 102a, 102a'.

Patient facing surface 111c of microwave spacer 100 (See FIG. 2) faces the patient and may be configured to facilitate contact with patient tissue. In one embodiment, a portion of the patient facing surface (e.g., patient facing surface 111c) includes a surface configured to aid in securing the microwave spacer 100 to patient tissue (i.e., a non-slip pattern formed in the housing body 111). In another embodiment, a portion of the patient facing surface 111c may include a coating or non-slip material configured to adhere to the patient, such as, for example, an adhesive coating, a non-skid cover or any other suitable surface or coating that aids in securing the microwave spacer 100 to the patient. In yet another embodiment, the microwave spacer 100 may include a plurality of appendages (i.e., feet and/or legs—not explicitly shown) or channels to elevate and/or space a portion of the patient facing surface 111c of the microwave spacer 100 with respect to patient tissue.

The height or thickness "H" of the microwave spacers 100, 300 is sufficient to securely guide the microwave energy delivery devices 10 such that the distal ends of the microwave energy delivery devices 10 are positioned in a desirable spaced apart relationship relative to each other (e.g., the spacing of the distal tips are desirably spaced apart and/or substantially equal)

Figure 4C:
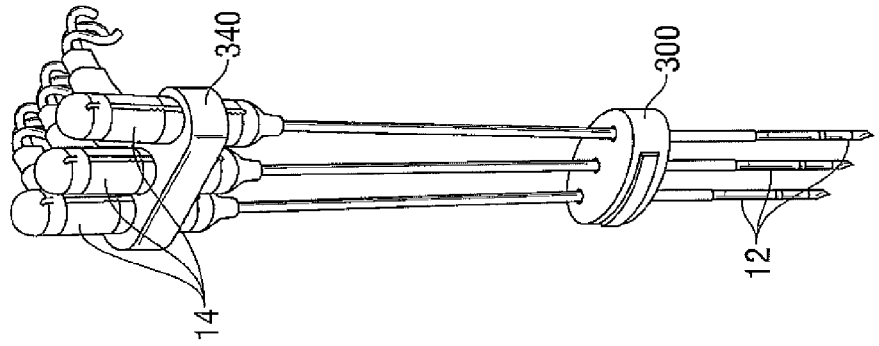
FIGS. 4A-4C are perspective views of another microwave spacer including first and second compression mechanisms in accordance with the present disclosure illustrating different configurations of a microwave energy delivery device including the use of a handle clamp.
Figure 4B:
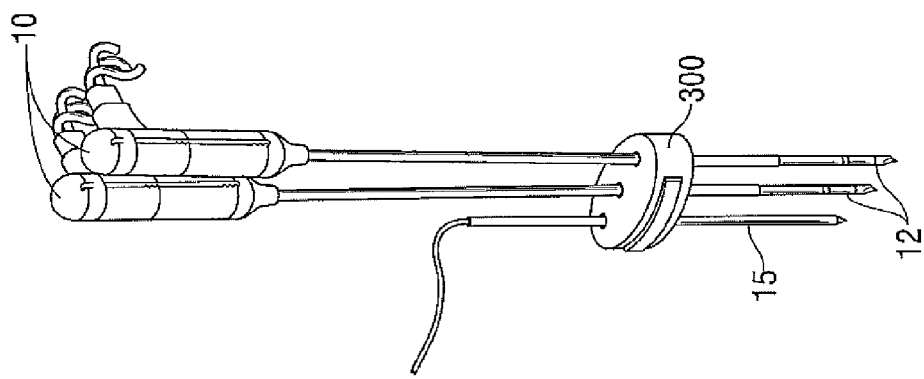
Figure 4A:
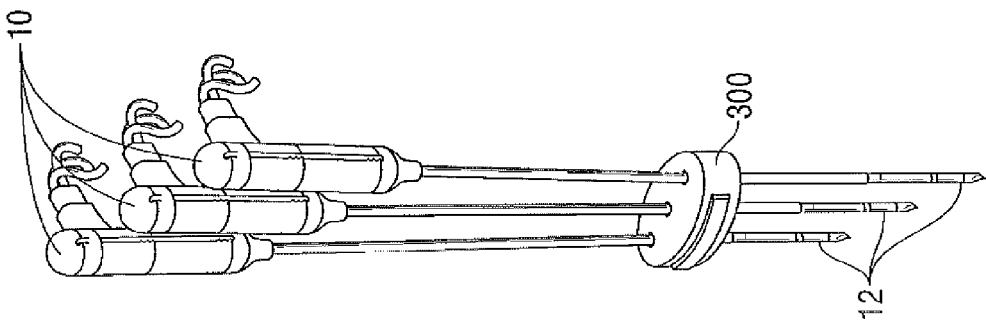

FIGS. 4A-4C are perspective views of a microwave spacer 300 that includes a first compression mechanism 316 and a second compression mechanism 317 independent of the first compression mechanism (see FIGS. 5A and 5B), in accordance with another embodiment of the present disclosure. FIG. 4A is a perspective view of the microwave spacer 300 positioning three microwave energy delivery devices 10 inserted therethrough in a straight-line configuration. FIG. 4B is a perspective view of the microwave spacer 300 positioning two microwave energy delivery devices 10 and a sensing device 15 therethrough. Sensing device 15 may include any device configured to measure a property of the target tissue such as, for example, a temperature (i.e., thermocouple, RTD or infrared heat measuring device), impedance and/or a tissue fluid content. Sensing device 15 may be inserted through an unused aperture pair (e.g. 102a, 102a' and 302a and 302a' in FIGS. 3 and 5a, respectively) in any of the microwave spacer 100, 300 described and illustrated herein. FIG. 4C is a perspective view of the microwave spacer 300 positioning three microwave energy delivery devices 10 therethrough and a handle clamp 340 that secures the handle portions 14 of the three microwave energy delivery devices 10.

Figure 5A:
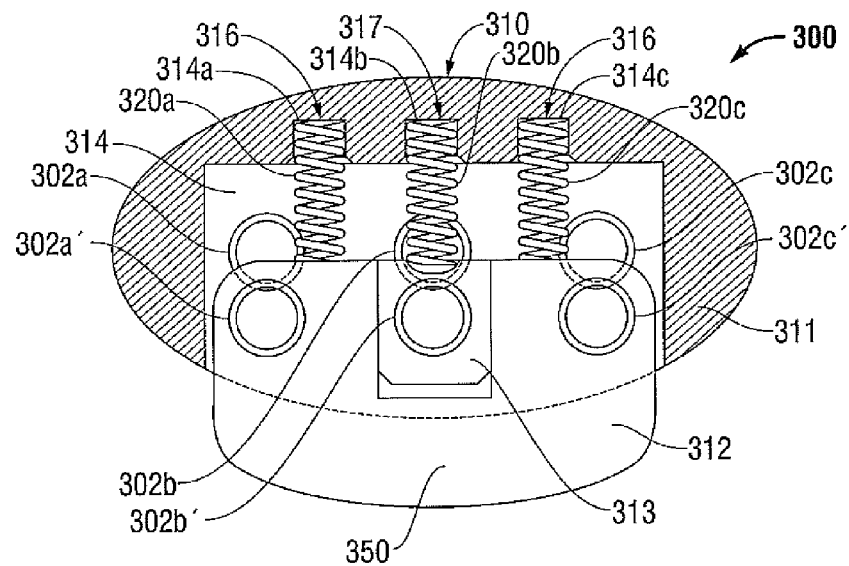
FIG. 5A is a top view of the microwave spacer of FIGS. 4A-4C in a first, substantially uncompressed configuration.
Figure 5B:
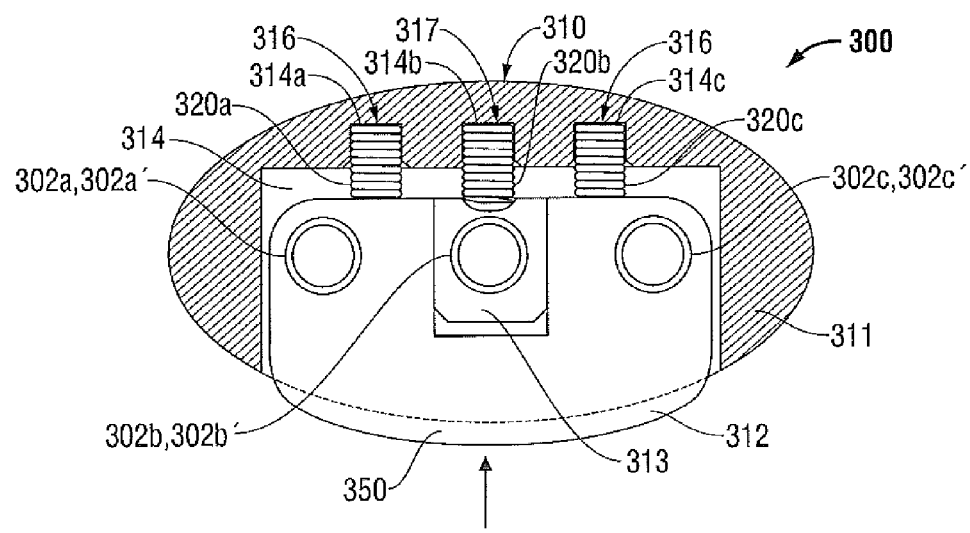
FIG. 5B is a top view of the microwave spacer of FIGS. 4A-4C in a second, substantially compressed configuration.
Figure 5C:
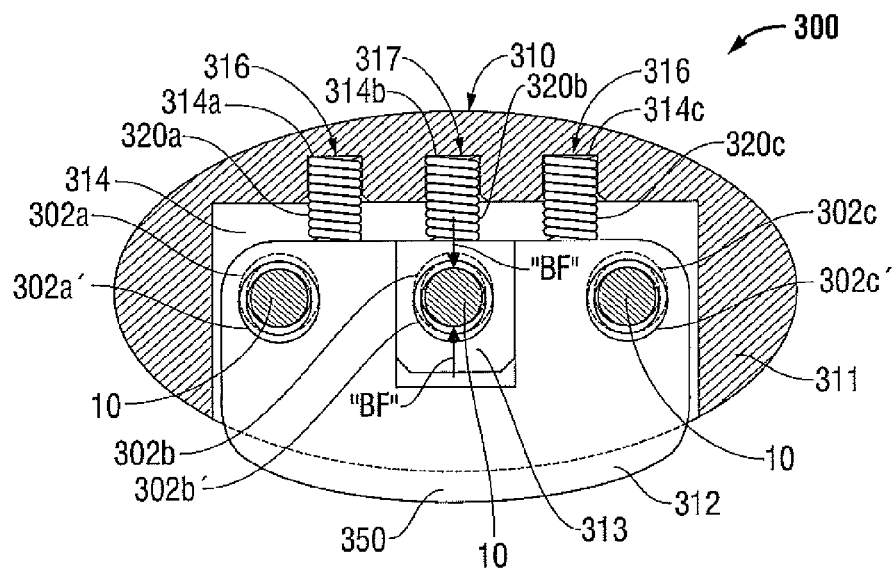
FIG. 5C is a top view of the microwave spacer of FIGS. 4A-4C in a third configuration wherein a static force is applied to microwave energy delivery devices inserted through the microwave spacer.

FIGS. 5A and 5B are perspective views of the microwave spacer 300 from FIGS. 4A-4C illustrating the first compression mechanism 316 and the second compression mechanism 317 that provide the compressible holding/locking mechanisms. More particularly, microwave spacer 300 includes a housing 310 including a housing body 311 and a compression body 312. The housing body 311 defines a housing body cavity 314 therein that slideably engages the compression body 312.

Housing 310 includes a retaining feature that retains the compression body 312 at least partially within the housing body cavity 314.

Figure 7A:
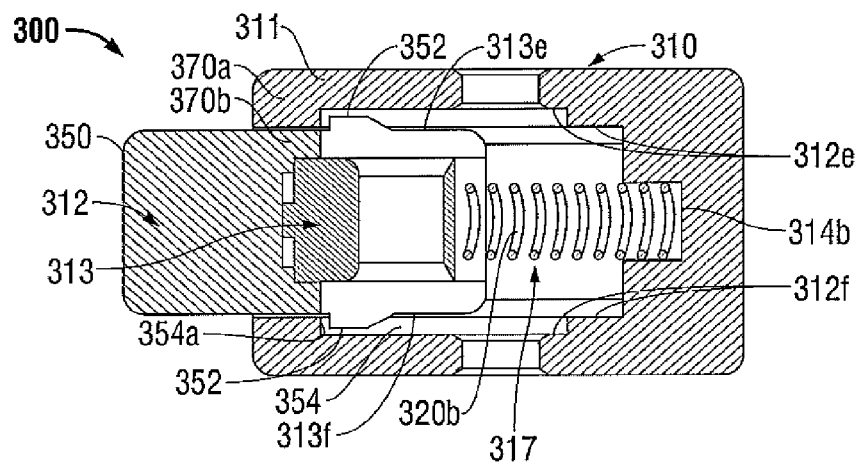
FIG. 7A is a cross-sectional view of the microwave spacer of FIG. 6 along line 7A-7A illustrating the mounting of the middle aperture spring-driven compression mechanism within the outer aperture spring-driven compression mechanism.

For example, the retaining feature includes press-fit tabs 352 formed on the compression body 312, as illustrated in FIG. 7A. Press-fit tabs may alternatively be formed on the housing body 311. Other retaining features and methods may be used to retain the compression body 312 within the housing body cavity 314.

Compression body 312 includes a compression body cavity 312a defined therein that slideably engages middle portion disposed within compression body 312. Middle portion 313 and compression body 312 are configured to move on the same plain with respect to the housing body 311.

Housing body 311 includes a plurality of outer housing device apertures 302a, 302c and a middle device aperture 302b defined therein and each configured to receive a microwave energy delivery device 10 therethrough. The outer housing device apertures 302a, 302c correspond to the compression body apertures 302a', 302c' formed in the compression body 312. The middle device aperture 302b corresponds to the middle device aperture 302b' formed in the middle portion 313.

Microwave spacer 300 includes a first compression mechanism 316, positioned between the housing body 311 and the compression body 312, and a second compression mechanism 317 positioned between the housing body 311 and the middle portion 313. The first compression mechanism 316 is configured to bias compression of the compression body 312 relative to the housing body cavity 314 and the second compression mechanism is configured to bias the middle portion 313 relative to the compression body cavity 312a.

As illustrated in FIGS. 5A, 5B and 5C, the first compression mechanism 316 include outer springs 320a, 320c positioned between the housing body 311 and the compression body 312. The second compression mechanism 317 includes the middle spring 320b positioned between the housing body 311 and the middle portion 313. Housing body 311 includes a plurality of spring apertures 314a, 314b, 314c, defined in the housing body cavity 314, each spring aperture 314a, 314b, 314c configured to house a first end of a corresponding compression spring 320a-322c. Compression springs 320a-322c bias the compression body 312 relative to the housing body 311 with the middle spring 320b biasing the middle portion 313 to a first position as illustrated in FIG. 5A. The first compression mechanism 316 and the second compression mechanism 317 may include a pneumatic pressure device, an elastic compression device, a resilient member, air bladder or any other suitable device that resists compression and provides resistance to the compression body 312 when driven into the housing body cavity 314.

Compression body 312 and middle portion 313 may be compressed to a second position (e.g., by compressing the outer springs 320a, 320c and the middle spring 320b, as illustrated in FIG. 5B). In the second position, the outer housing device apertures 302a, 302c, align with the respective compression body apertures 302a', 302c' and the middle device aperture 302b aligns with the middle device aperture 302b' thereby facilitating the insertion of a microwave energy delivery device 10 through one or more selected aperture pairs 302a and 302a', 302b and 302b', 302c and 302c'. In a second position, a microwave energy delivery devices 10 moves freely through any one of the apertures pairs 302a and 302a', 302b and 302b', 302c and 302c' formed in the microwave spacer 300.

With reference to FIGS. 5A and 5B, the outer portion 350 of compression body 312 is about equal to the distance of travel of the compression body 312 between the first position, as illustrated in FIG. 5A, and the second position, as illustrated in FIG. 5B. In the second condition, the outer portion 350 of the compression body extends beyond the housing body 311 by at least 0.05".

As illustrated in FIG. 5C, compression body 312, when released from the second position with one or more microwave energy delivery devices 10 positioned in an aperture pair 302a and 302a', 302b and 302b', 302c and 302c', is driven by the outer springs 320a, 320c toward the first position and contact the microwave energy delivery devices 10 in outer housing device apertures 302a, 302e in a third position. Similarly, middle portion 313 is driven by middle spring 320b and contacts a microwave energy delivery device 10 in the middle aperture pair (e.g., 302b, 302b') in a third position. The compression body 312 and/or the middle portion 313 apply a biasing force (or compression force) to a portion of a microwave energy delivery device 10 as illustrated by arrows "BF". The biasing force applied to the microwave energy delivery devices 10 lock and/or hold the microwave energy delivery device 10 in a fixed position with respect to the microwave spacer 100.

In another embodiment, the compression body 312 and the housing body 311 may apply a first biasing force to the microwave energy delivery devices 10 inserted in the outer aperture pairs 302a, 302a', 302c and 302c' and the middle portion 313 and the housing body 311 may apply a second biasing static force to the microwave energy delivery device 10 inserted in the middle portion aperture pair 302b, 302b'. The first biasing force may be evenly divided between the microwave energy delivery devices 10 inserted into each of the outer aperture pairs 302a, 302a', 302c and 302c' and/or may be substantially equal to the second biasing force applied to the microwave energy delivery device 10 inserted in the middle portion aperture pair 302b, 302b'. In yet another embodiment, the biasing force applied to each microwave energy delivery device 10 (e.g., the portion of the first biasing force applied to each microwave energy delivery device 10 and the second biasing force) may not be substantially equal.

The biasing force applied to each microwave energy delivery device 10 positioned any one of the aperture pairs 302a and 302a', 302b and 302b', 302c and 302c' of the microwave spacer 300 may be released by re-positioning the compression body 312 to the second position (as illustrated in FIG. 5B). After repositioning the biasing forces, the microwave energy delivery device 10 may be withdrawn from the microwave spacer 300.

In yet another embodiment, the biasing force applied by the microwave spacer 100, 300 to the microwave energy delivery devices 10 may be maintained and the microwave spacer 100, 300 may be used to simultaneously withdraw the microwave energy delivery devices 10 from patient tissue. As such, the biasing force applied to each microwave energy delivery device 10 to maintain the position with respect to the microwave spacer 100, 300 must be greater than the force required to withdraw the microwave energy delivery devices 10 from patient tissue.

Figure 6:
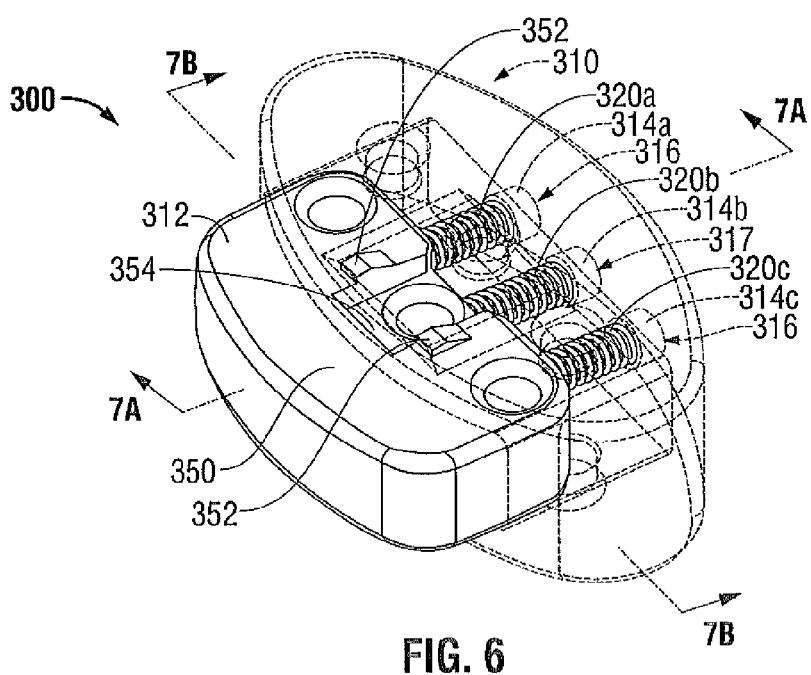
FIG. 6 is a perspective view of the microwave spacer of FIG. 5A illustrating the internal components of the first compression mechanism and the second compression mechanisms including spring-driven compression mechanisms.

FIG. 6 is a perspective view of the microwave spacer 300 of FIGS. 5A-5C further illustrating the internal components of the first and second compression mechanisms. The first compression mechanism 316 that biases the compression body 312 includes outer springs 320a, 320c. The second compression mechanism 317 that biases the middle portion 313 includes the middle spring 320b. Outer springs 320a, 320c are under compression and apply a biasing force to the compression body 312 throughout the range of movement of the compression body 312 within the housing body cavity 314. In a first position, the springs 320a-320c are extended and the outer portion 350 of the compression body 312 extends beyond the housing body 311.

Figure 7B:
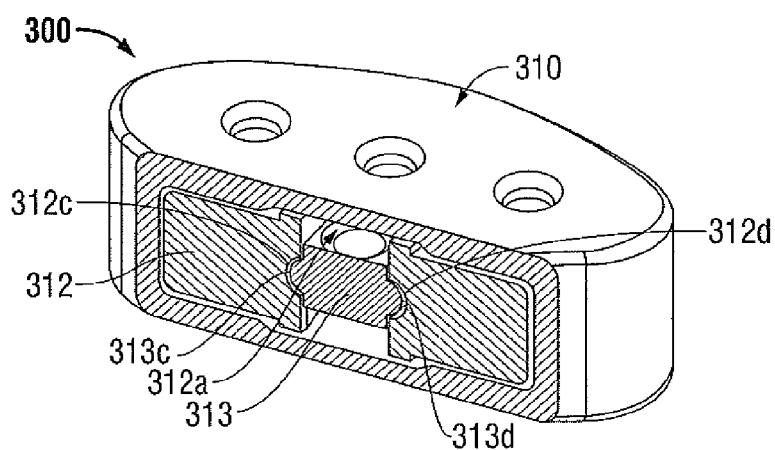
FIG. 7B is a cross-sectional view of the microwave spacer of FIG. 6 along 7B-7B illustrating the slidable interface between the middle aperture spring-driven compression mechanism and the outer aperture spring-driven compression mechanism.

As illustrated in FIGS. 7A and 7B, at least a portion of the compression body 312 is retained within the housing body cavity 314 while slideably engaging the housing body 311 as mentioned above. Microwave spacer 300 includes a retaining feature (e.g., press fit tabs) configured to retain the compression body 312 within the housing body cavity 314. For example, one or more press-fit tabs 352, formed in the compression body 312, may interlock with an undercut 354, formed in the housing body 311. The press-fit tabs 352 slide in a substantially unrestricted fashion within the undercut 354 portion of the housing body 311. In a first position, the undercut edge 354a of the undercut 354 is a catch surface for the press-fit tabs 352 thereby restricting the movement of the compression body 312 within the housing body cavity 314.

The retaining feature may include one or more structures, on the compression body 312 and/or the housing body 311, that maintains the compression body 312 slideably engaged within the housing body cavity 314. For example, the positioning dowels 115a, 115b and dowel slot 116a, 116b arrangement, as illustrated and described hereinabove (see FIG. 3), may be used to retain and/or guide the compression body 312 within the housing body cavity 314.

In another embodiment, the retaining feature includes a raised structure (not explicitly shown) formed in the housing body 311 that slideably engages a corresponding channel (not explicitly shown) wherein the engagement of the raised structure with the channel defines and/limits the range of movement between the compression body 312 and the housing body 311. Microwave spacer 300 may include a plurality of raised portions and corresponding channels formed on the housing body 311 and compression body 312.

With reference to FIGS. 6 and 7A, the microwave spacer 300 is assembled by positioning each spring 320a, 320b, 320c in the corresponding spring aperture 314a, 314b, 314c formed in the housing body cavity 314. The compression body assembly, which includes the middle portion 313 positioned in the compression body cavity 312a of the compression body 312, is inserted into the housing body cavity 314. During insertion, the press-fit tabs 352 engage the housing body 311 between the opening of the housing body cavity 314 and the undercut 354. The press-fit tabs 352 press against the housing body 311 causing at least a portion of the housing body 311 to flex outwardly. The housing body 311 returns to the pre-flexed condition after the press-fit tabs 352 engage the undercut 354.

Disassembly the microwave spacer 300 (e.g., removing the compression body 312 from the housing body 311) requires the housing body 311 to flex outwardly such that the press-fit tabs 352 do not engage the undercut edge 354a of the undercut 354.

FIG. 7A is cross-sectional view of the microwave spacer 300 of FIG. 6 illustrating the positioning of the middle portion 313 with respect to the compression body 312. Top horizontal surface 313e and bottom horizontal surface 313f of the middle portion 313 are offset from the top horizontal surface 312e and bottom horizontal surface 312f of the compression body cavity 312a to avoid interference between the middle portion 313 and any portion of the compression body cavity 312a. Middle spring 320b is positioned in the spring aperture 314b between the housing body 311 and the compression body 312 and is at least partially compressed through the range of movement of the middle portion 313.

FIG. 7B further illustrates the assembly of the middle portion 313 within the compression body cavity 312a. Middle portion 313 includes a first guide 313c and a second guide 313d on opposing vertical side edges. The first guide 313c and second guide 313d slidably engage corresponding first slot 312c and second slot 312d, respectively, formed in the compression body 312 on opposing vertical side walls of the compression body cavity 312a.

In a first position, as described hereinabove and illustrated in FIGS. 5A and 6, the middle portion 313 is driven inwardly within the compression body cavity 312a by the middle spring 320b. When repositioned from a first position to a second position, the compression body 312 presses against the middle portion 313, which, in turn, compresses the middle spring 320b. After a microwave energy delivery device 10 is positioned in the middle portion aperture pair 302b, 302b', and the compression body 112 is released, as described hereinabove, the middle portion 313 applies a biasing force (e.g., compression force) to a portion of a microwave energy delivery device 10 positioned in the middle portion aperture pair 302b, 302b'. A biasing force, applied to the microwave energy delivery device 10 by both the middle portion 313 and the housing body 311, lock and/or hold the microwave energy delivery device 10 inserted through the middle portion aperture pair 302b, 302b' in a fixed position with respect to the microwave spacer 100.

Figure 8:
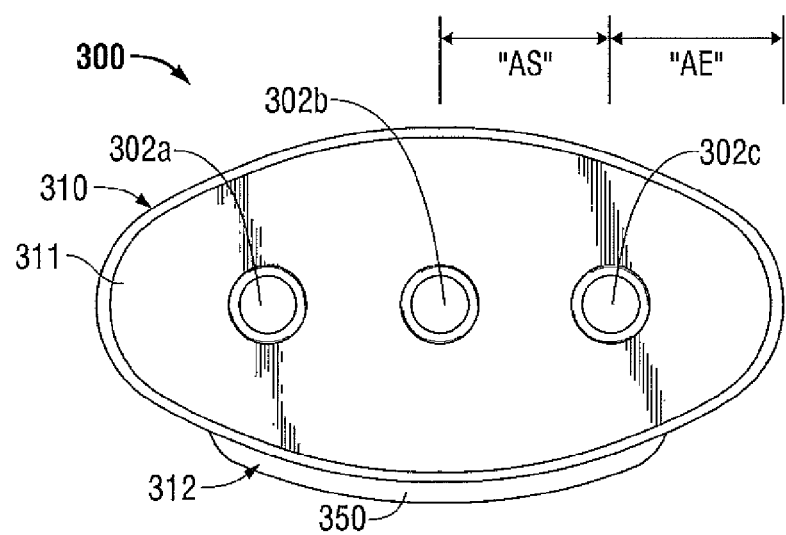
FIG. 8 is a top, perspective view the microwave spacer of FIG. 6, in a compressed configuration illustrating one spacing arrangement of the present disclosure.

FIG. 8 is a top, perspective view of the microwave spacer 300 of FIG. 6, in a compressed configuration illustrating one spacing arrangement of the present disclosure. As described herein, the microwave spacers 100, 300 are configured to guide a microwave energy delivery device 10 during the insertion step of a surgical procedure. The microwave spacers 100, 300 aid in providing consistent spacing between adjacent microwave energy delivery devices 10 and assist in maintaining parallelism between the devices during and after insertion. As such, the spacing between adjacent apertures is directly related, if not substantially equal to, the spacing between the antennas 12 positioned at the distal end of each microwave energy delivery devices 10.

In one particular embodiment, adjacent aperture spacing "AS" is equal to about 1 cm and the aperture to edge spacing "AE" is equal to about 1 cm. The aperture to edge spacing "AE" provides a reference spacing about equal to the adjacent aperture spacing "AS" for successive ablations. In another embodiment, the aperture to edge spacing "AE" is about equal to half the adjacent aperture spacing "AS" such that side-by-side placement of microwave spacers results in the spacing between adjacent outer apertures on the adjacent microwave spacers is substantially equal to the adjacent aperture spacing "AS".

A portion of the outer portion 350 of the compression body 312 may extend beyond the housing body 311. In one embodiment the outer portion 350 may extend a minimum of about 0.05 inches from the housing body 311.

Microwave spacers 100, 300 according to the present disclosure may be constructed from material capable of withstanding temperatures generated by the particular microwave ablation procedure. The spacer may be formed from a non-conductive plastic material, such as, for example, plastic (i.e., polyethylene terephthalate, polystyrene, rubber, polycarbonate, polytetrafluoroethylene or polyimide), ceramic, carbon fiber, or any other suitable non-conductive material. Spacer may also be formed from a conductive material, such as, for example, aluminum or stainless steel. A spacer formed from a conductive material may result in heating and may further include active or passive cooling. For example, the spacer may include a heat exchanger or may form cooling fins, air circulation channels or fluid cooling ports and channels.

In use, a microwave spacer 100, 300 is placed on patient tissue adjacent a target tissue or tissue targeted for a medical procedure, (i.e., an ablation procedure, a resection procedure or any other suitable electrosurgical procedure that requires electrosurgical energy delivery). The clinician may utilize an imaging/positioning system, such as, for example, an ultrasonic system, an x-ray system a CT scan system or any other suitable imaging/positioning system (not explicitly shown) to determine proper positioning of the microwave spacer 100, 300 with respect to the target tissue. A compressive force, when applied to the compression body 112, 312 and housing body 111, 311 aligns corresponding pair of apertures (e.g., 102a and 102a', 302a and 302a') formed in the housing body 111, 311 and in the compression body 112, 312. Two or more microwave energy delivery devices 10 are inserted into a corresponding number of selected aligned aperture pairs (i.e., 102a and 102a', 302a and 302a'). The imaging system (not explicitly shown) may be used during the insertion step to determine when each microwave energy delivery device 10 is properly positioned in target tissue. When the compressive force that positioned the compression body 112, 312 in the second position is removed, a biasing force is applied to at least the portion of the microwave energy delivery devices 10 between the compression body 112, 312 and the housing body 111, 311. Aperture pairs (e.g., 102a, 102a' and 302a, 302a') not used for the insertion of microwave energy delivery devices 10 may be used for the placement of other probes or sensors (not explicitly shown), such as, for example, one or more temperature probes or sensors.

A method for placing a plurality of microwave energy delivery devices 10 for ablating tissue is also provided by the present invention and includes the steps of placing the microwave spacer 100, 300 including a housing body 111, 311 that slideably engages a compression body 112, 312, on a portion of patient tissue adjacent a target tissue; compressing the microwave spacer 100, 300 to align apertures (e.g., 102a, 102b, 102c and 302a, 302b, 302c) formed by the housing body 111, 311, respectively, and apertures (e.g., 102a', 102b', 102c' and 302a', 302b', 302c') formed by the compression body 112, 312, respectively; inserting two or more microwave energy delivery devices 10 through aligned aperture pairs (e.g., 102a and 102a', 302a and 302a') and into the target tissue; uncompressing or otherwise removing the compressive force on the compression body 112, 312 relative to the housing body 111, 311 thereby apply a biasing force to the microwave energy delivery devices 10; connecting the two or more microwave energy delivery devices 10 to a microwave energy source (not explicitly shown); and ablating the target tissue by delivering microwave energy through the microwave energy delivery devices 10.

Another method for placing a plurality of microwave energy delivery devices 10 and ablating tissue includes the steps of: placing the microwave spacer 100, 300 including a housing body 111, 311 that slideably engages a compression body 112, 312, on a portion of patient tissue adjacent a target tissue; applying a compressive force to align apertures (e.g., 102a, 102a' and 302a, 302a') formed in the housing body 111, 311 and compression body 112, 312; placing a microwave energy delivery device 10 through an aligned pair of aperture (e.g., 102a, 102a' and 302a, 302a'); advancing an antenna 12 of microwave energy delivery devices 10 to the target tissue; inserting another microwave energy delivery device 10 through a pair of aligned aperture (e.g., 102a, 102a' and 302a, 302a') and into the target tissue; releasing the compressive force on the microwave spacer 100, 300; connecting the microwave energy delivery devices 10 to a microwave energy source; and ablating the target tissue by delivering microwave energy through the microwave energy delivery devices 10.

The methods may further include the step of inserting one or more sensing devices 15 through a pair of aligned apertures (e.g., 102a, 102a' and 302a, 302a') and into the target tissue. The sensing device 15 may include a device configured to measure a property of the target tissue such as, for example, a temperature (i.e., thermocouple, RTD or infrared heat measuring device), impedance and/or a tissue fluid content.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A spacer configured to position microwave energy delivery devices including:
    a housing including:
        a housing body forming a housing body cavity and a plurality of housing device apertures;
        a compression body forming a plurality of compression body apertures that each correspond to one of the plurality of housing device apertures, the compression body configured to slideably engage the housing body cavity, wherein at least a portion of the compression body is positioned in the housing body cavity; and
    a first compression mechanism, positioned between the housing body and the compression body, the first compression mechanism configured to provide a biasing force between the compression body and the housing body,
    wherein in a first position a portion of the compression body extends a first distance beyond the body housing and the plurality of housing device apertures are misaligned with the plurality of compression body apertures and in a second position the plurality of housing device apertures are aligned with the plurality of compression body apertures and forming a plurality of aligned aperture pairs configured to receive a microwave energy delivery device therethrough.

2. The spacer according to claim 1, wherein in a third position the housing body and the compression body apply a first biasing force, generated from the first compression mechanism, to the microwave energy delivery device positioned through one of the plurality of aligned aperture pairs.

3. The spacer according to claim 2, wherein in the third position the compression body extends a second distance beyond the housing body, the second distance being less than the first distance.

4. The spacer according to claim 2, wherein the first compression mechanism further includes:
    at least one spring positioned between the compression body and the housing body wherein in the first position the at least one spring is substantially uncompressed and in the second position the at least one spring is substantially compressed.

5. The spacer according to claim 1, further including:
    a compression body cavity formed in the compression body;
    a middle portion, forming a middle device aperture, configured to slideably engage the compression body cavity, and
    a second compression mechanism, positioned between the middle portion and the housing body, the second compression mechanism configured to provide a second biasing force between the middle portion and the housing body, and
    wherein in the first position the plurality of housing device apertures are misaligned with the middle device aperture and in the second position at least one of the plurality of housing device apertures aligns with the middle device aperture thereby forming a middle device aperture configured to receive the microwave energy delivery device therethrough.

6. The spacer according to claim 5, wherein the first compression mechanism further includes at least one first compression mechanism spring positioned between the compression body and the housing body wherein in the first position the at least one first compression mechanism spring is substantially uncompressed and in the second position the at least one first compression mechanism spring is substantially compressed.

7. The spacer according to claim 6, wherein the second compression mechanism further includes at least one second compression mechanism spring positioned between the housing body and the middle portion wherein in the first position the at least one second compression mechanism spring is substantially uncompressed and in the second position the at least one second compression mechanism spring is substantially compressed.

8. The spacer according to claim 7 wherein in a third position the housing body and the compression body are configured to apply a first biasing force to the microwave energy delivery device positioned through one of the plurality of aligned aperture pairs and,
    wherein the housing body and the middle portion are configured to apply a second biasing force to the microwave energy delivery device positioned through the middle device aperture.

9. The spacer according to claim 5, wherein the first compression mechanism further includes two first compression mechanism springs positioned between the compression body and the housing body and the second compression mechanism further includes at least one second compression mechanism spring positioned between the housing body and the middle portion wherein in the first position the at least one second compression mechanism spring and the two first compression mechanism springs are substantially uncompressed and in the second position the at least one second compression mechanism spring and the two first compression mechanism springs are substantially compressed.

10. The spacer according to claim 9, wherein in a third position the housing body and the compression body are configured to apply a first biasing force to the microwave energy delivery device positioned through one of the plurality of aligned aperture pairs and the housing body and the middle portion are configured to apply a second biasing force to the microwave energy delivery device positioned through the middle device aperture.

11. The spacer according to claim 10, wherein the first biasing force and the second biasing force are not equal.

12. A spacer configured to position microwave energy delivery devices, the spacer comprising:
a housing including:
a housing body defining a housing body cavity and a plurality of housing device apertures;
a compression body defining a compression body cavity and a plurality of compression body apertures that each correspond to one of the plurality of housing device apertures, the compression body configured to slideably engage the housing body cavity, wherein at least a portion of the compression body is positioned in the housing body cavity;
a middle portion forming a middle device aperture, configured to slideably engage the compression body cavity;
a first compression mechanism positioned between the housing body and the compression body, the first compression mechanism configured to provide a biasing force between the compression body and the housing body; and
a second compression mechanism positioned between the middle portion and the housing body, the second compression mechanism configured to provide a second biasing force between the middle portion and the housing body,
wherein in a first position a portion of the compression body extends a first distance beyond the body housing and the plurality of housing device apertures are misaligned with the plurality of compression body apertures and the middle device aperture and in a second position the plurality of housing device apertures are aligned with the plurality of compression body apertures and the middle device aperture thereby forming a plurality of aligned aperture pairs configured to receive a microwave energy delivery device therethrough.

13. The spacer according to claim 12, wherein the first compression mechanism further includes at least one first compression mechanism spring positioned between the compression body and the housing body wherein in the first position the at least one first compression mechanism spring is substantially uncompressed and in the second position the at least one first compression mechanism spring is substantially compressed.

14. The spacer according to claim 13, wherein the second compression mechanism further includes at least one second compression mechanism spring positioned between the housing body and the middle portion wherein in the first position the at least one second compression mechanism spring is substantially uncompressed and in the second position the at least one second compression mechanism spring is substantially compressed.

15. The spacer according to claim 14 wherein in a third position the housing body and the compression body are configured to apply a first biasing force to the microwave energy delivery device positioned through one of the plurality of aligned aperture pairs and,
wherein the housing body and the middle portion are configured to apply a second biasing force to the microwave energy delivery device positioned through the middle device aperture.

16. The spacer according to claim 15, wherein in the third position the compression body extends a second distance beyond the housing body, the second distance being less than the first distance.

17. The spacer according to claim 12, wherein the first compression mechanism further includes two first compression mechanism springs positioned between the compression body and the housing body and the second compression mechanism further includes at least one second compression mechanism spring positioned between the housing body and the middle portion wherein in the first position the at least one second compression mechanism spring and the two first compression mechanism springs are substantially uncompressed and in the second position the at least one second compression mechanism spring and the two first compression mechanism springs are substantially compressed.

18. The spacer according to claim 17, wherein in a third position the housing body and the compression body are configured to apply a first biasing force to the microwave energy delivery device positioned through one of the plurality of aligned aperture pairs and the housing body and the middle portion are configured to apply a second biasing force to the microwave energy delivery device positioned through the middle device aperture.

19. The spacer according to claim 18, wherein the first biasing force and the second biasing force are not equal.

* * * * *